US008238646B2

(12) United States Patent
Floeder et al.

(10) Patent No.: US 8,238,646 B2
(45) Date of Patent: *Aug. 7, 2012

(54) APPARATUS AND METHOD FOR THE AUTOMATED MARKING OF DEFECTS ON WEBS OF MATERIAL

(75) Inventors: Steven P. Floeder, Shoreview, MN (US); James A. Masterman, Lake Elmo, MN (US); Carl J. Skeps, Lakeville, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/102,434

(22) Filed: May 6, 2011

(65) Prior Publication Data

US 2011/0211747 A1 Sep. 1, 2011

Related U.S. Application Data

(63) Continuation of application No. 12/581,421, filed on Oct. 19, 2009, now Pat. No. 7,974,459, which is a continuation of application No. 10/826,995, filed on Apr. 19, 2004, now Pat. No. 7,623,699.

(51) Int. Cl.
  *G06K 9/00* (2006.01)
(52) U.S. Cl. ........ 382/149; 382/100; 382/111; 382/112; 382/141; 382/151; 700/122; 700/124; 700/125
(58) Field of Classification Search ................... 382/100, 382/103, 111, 112, 141, 143–152, 325; 700/122–129, 143, 144
See application file for complete search history.

(56) References Cited

U.S. PATENT DOCUMENTS

| 3,759,620 A | 9/1973 | Cushing et al. |
| 4,134,684 A | 1/1979 | Jette |
| 4,173,441 A | 11/1979 | Wolf |
| 4,211,132 A | 7/1980 | Nichols, III et al. |
| 4,330,356 A | 5/1982 | Grollimund et al. |
| 4,458,852 A | 7/1984 | Calvert et al. |
| 4,567,064 A | 1/1986 | Woste |
| 4,583,181 A * | 4/1986 | Gerber et al. ................. 700/143 |
| 4,629,312 A | 12/1986 | Pearce et al. |
| 4,700,627 A | 10/1987 | Hagler |
| 4,746,020 A | 5/1988 | Schenk |
| 4,752,897 A | 6/1988 | Zoeller et al. |
| 4,776,023 A | 10/1988 | Hamada et al. |

(Continued)

FOREIGN PATENT DOCUMENTS

EP  0 584 637 A2  3/1994

(Continued)

OTHER PUBLICATIONS

Brian Tithecott, "Flexible Circuits, Roll-to-Roll AOI" PC FAB, vol. 23, No. 2, Feb. 2000, pp. 26-32.*

(Continued)

*Primary Examiner* — Matthew Bella
*Assistant Examiner* — Eric Rush
(74) *Attorney, Agent, or Firm* — Steven A. Bern

(57) ABSTRACT

A system for the characterization of webs that permits the identification of anomalous regions on the web to be performed at a first time and place, and permits the localization and marking of actual defects to be performed at a second time and place.

5 Claims, 2 Drawing Sheets

U.S. PATENT DOCUMENTS

| | | | |
|---|---|---|---|
| 4,828,156 A | 5/1989 | Whiteley et al. | |
| 4,877,323 A | 10/1989 | Stillwagon | |
| 4,905,159 A | 2/1990 | Loriot | |
| 4,927,180 A | 5/1990 | Trundle et al. | |
| 4,951,223 A | 8/1990 | Wales et al. | |
| 4,972,326 A | 11/1990 | Jung et al. | |
| 4,982,600 A | 1/1991 | Kiso et al. | |
| 5,062,331 A | 11/1991 | Michal et al. | |
| 5,068,799 A | 11/1991 | Jarrett, Jr. | |
| 5,301,129 A | 4/1994 | McKaughan et al. | |
| 5,305,392 A | 4/1994 | Longest, Jr. et al. | |
| 5,351,202 A | 9/1994 | Kurtzberg et al. | |
| 5,365,596 A * | 11/1994 | Dante et al. | 382/141 |
| 5,403,722 A | 4/1995 | Floeder et al. | |
| 5,415,123 A | 5/1995 | Ryder | |
| 5,434,629 A | 7/1995 | Pearson et al. | |
| 5,439,871 A | 8/1995 | Matoushek | |
| 5,440,648 A | 8/1995 | Roberts et al. | |
| 5,450,116 A | 9/1995 | Weiselfish et al. | |
| 5,533,145 A * | 7/1996 | Shofner et al. | 382/141 |
| 5,544,256 A | 8/1996 | Brecher et al. | |
| 5,696,591 A | 12/1997 | Bilhorn et al. | |
| 5,710,420 A | 1/1998 | Martin et al. | |
| 5,760,414 A | 6/1998 | Taylor | |
| 5,774,177 A | 6/1998 | Lane | |
| 5,873,392 A | 2/1999 | Meyer et al. | |
| 5,922,168 A | 7/1999 | Zablotny et al. | |
| 5,949,550 A | 9/1999 | Arndt et al. | |
| 6,014,209 A | 1/2000 | Bishop | |
| 6,031,931 A | 2/2000 | Chiu et al. | |
| 6,092,059 A | 7/2000 | Straforini et al. | |
| 6,100,989 A | 8/2000 | Leuenberger | |
| 6,137,967 A | 10/2000 | Laussermair et al. | |
| 6,252,237 B1 | 6/2001 | Ramthun et al. | |
| 6,259,109 B1 * | 7/2001 | Dalmia et al. | 250/559.08 |
| 6,266,436 B1 | 7/2001 | Bett et al. | |
| 6,266,437 B1 | 7/2001 | Eichel et al. | |
| 6,272,437 B1 | 8/2001 | Woods et al. | |
| 6,295,129 B1 | 9/2001 | Björk | |
| 6,314,379 B1 | 11/2001 | Hu et al. | |
| 6,330,350 B1 | 12/2001 | Ahn et al. | |
| 6,359,447 B1 | 3/2002 | Sighinolfi | |
| 6,359,477 B1 | 3/2002 | Pathak | |
| 6,404,910 B1 | 6/2002 | Ungpiyakul et al. | |
| 6,407,373 B1 | 6/2002 | Dotan | |
| 6,452,679 B1 | 9/2002 | Workman, Jr. | |
| 6,479,228 B2 | 11/2002 | Majumdar et al. | |
| 6,484,306 B1 | 11/2002 | Bokor et al. | |
| 6,496,596 B1 | 12/2002 | Zika et al. | |
| 6,661,507 B2 | 12/2003 | Yoda et al. | |
| 6,665,432 B1 | 12/2003 | Evans et al. | |
| 6,750,466 B2 | 6/2004 | Guha et al. | |
| 6,765,224 B1 | 7/2004 | Favreau et al. | |
| 6,778,694 B1 | 8/2004 | Alexandre | |
| 6,798,925 B1 | 9/2004 | Wagman | |
| 6,804,381 B2 | 10/2004 | Pang et al. | |
| 6,812,997 B2 | 11/2004 | Kaltenbach et al. | |
| 6,814,514 B2 | 11/2004 | Korngold et al. | |
| 6,845,278 B2 | 1/2005 | Popp et al. | |
| 6,903,726 B1 | 6/2005 | Bock | |
| 6,934,028 B2 | 8/2005 | Ho et al. | |
| 6,950,547 B2 | 9/2005 | Floeder et al. | |
| 7,006,674 B1 | 2/2006 | Zahniser et al. | |
| 7,027,934 B2 | 4/2006 | Skeps et al. | |
| 7,117,057 B1 | 10/2006 | Kuo et al. | |
| 7,120,515 B2 | 10/2006 | Floeder et al. | |
| 7,146,034 B2 | 12/2006 | Reeves et al. | |
| 7,172,124 B2 | 2/2007 | Wang et al. | |
| 7,187,995 B2 | 3/2007 | Floeder et al. | |
| 7,248,366 B2 | 7/2007 | Uesugi et al. | |
| 7,542,821 B2 | 6/2009 | Floeder et al. | |
| 7,623,699 B2 | 11/2009 | Floeder et al. | |
| 7,797,133 B2 | 9/2010 | Floeder et al. | |
| 7,831,317 B2 | 11/2010 | McGreevy et al. | |
| 2001/0030749 A1 | 10/2001 | Ho et al. | |
| 2002/0019112 A1 | 2/2002 | Farrar | |
| 2002/0020704 A1 | 2/2002 | Zacharias | |
| 2002/0030704 A1 * | 3/2002 | Korngold et al. | 347/1 |
| 2002/0039436 A1 | 4/2002 | Alumot et al. | |
| 2002/0080347 A1 | 6/2002 | Yoda et al. | |
| 2002/0082739 A1 | 6/2002 | Nakata et al. | |
| 2002/0109112 A1 | 8/2002 | Guha et al. | |
| 2002/0110269 A1 | 8/2002 | Floeder et al. | |
| 2002/0176617 A1 | 11/2002 | Simonette | |
| 2003/0025027 A1 | 2/2003 | Ebisawa et al. | |
| 2003/0081219 A1 | 5/2003 | Bennett | |
| 2003/0189704 A1 | 10/2003 | Floeder et al. | |
| 2004/0030432 A1 | 2/2004 | Popp | |
| 2004/0030435 A1 | 2/2004 | Popp et al. | |
| 2004/0039435 A1 | 2/2004 | Hancock et al. | |
| 2004/0058540 A1 | 3/2004 | Matsumoto et al. | |
| 2005/0075801 A1 | 4/2005 | Skeps et al. | |
| 2005/0092839 A1 | 5/2005 | Oram | |
| 2005/0141760 A1 | 6/2005 | Floeder et al. | |
| 2005/0144094 A1 | 6/2005 | Floeder et al. | |
| 2005/0154485 A1 | 7/2005 | Popp et al. | |
| 2005/0232475 A1 | 10/2005 | Floeder et al. | |
| 2006/0055398 A1 | 3/2006 | Kuroyanagi et al. | |
| 2006/0066398 A1 | 3/2006 | Akamine et al. | |
| 2006/0164645 A1 | 7/2006 | Hietanen et al. | |
| 2009/0028416 A1 | 1/2009 | Floeder et al. | |
| 2009/0028417 A1 | 1/2009 | Floeder et al. | |
| 2009/0030544 A1 | 1/2009 | Floeder et al. | |
| 2010/0040278 A1 | 2/2010 | Floeder et al. | |

FOREIGN PATENT DOCUMENTS

| | | |
|---|---|---|
| EP | 0 681 183 A2 | 11/1995 |
| EP | 0 898 163 A1 | 2/1999 |
| EP | 1 022 906 | 7/2000 |
| EP | 1 348 946 A1 | 10/2003 |
| JP | 53-084793 | 7/1978 |
| JP | 59-138904 | 8/1984 |
| JP | 62/093637 | 4/1987 |
| JP | 04-004865 | 1/1992 |
| JP | 05-196581 | 8/1993 |
| JP | 06-071864 | 3/1994 |
| JP | 06-182444 | 7/1994 |
| JP | 07-024528 | 1/1995 |
| JP | 08-103976 | 4/1996 |
| JP | 08-189904 | 7/1996 |
| JP | 11/248641 | 9/1999 |
| JP | 2000/009447 | 1/2000 |
| JP | 2000/051940 | 2/2000 |
| JP | 2001/261191 | 9/2001 |
| JP | 2001/347315 | 12/2001 |
| JP | 2002-192230 | 7/2002 |
| JP | 2002/236015 | 8/2002 |
| JP | 2002/243648 A | 8/2002 |
| JP | 2003/084822 | 3/2003 |
| JP | 2003/166940 | 6/2003 |
| KR | 10-0655567 | 12/2006 |
| WO | WO 95/14805 | 6/1995 |
| WO | WO 98/44336 | 10/1998 |
| WO | WO 99/10833 | 3/1999 |
| WO | WO 00/07031 | 2/2000 |
| WO | WO 01/02840 A1 | 1/2001 |
| WO | WO 01/53811 A1 | 7/2001 |
| WO | WO 02/21105 A2 | 3/2002 |
| WO | WO 02/65106 A1 | 8/2002 |
| WO | WO 02/65107 A2 | 8/2002 |
| WO | WO 03/081219 A1 | 10/2003 |
| WO | WO 2005/065367 A2 | 7/2005 |
| WO | WO 2005/106104 A1 | 11/2005 |
| WO | WO 2006/066398 A1 | 6/2006 |
| WO | WO 2007/026174 A2 | 3/2007 |

OTHER PUBLICATIONS

"A PC-Based Real Time Defect Imaging System for High Speed Web Inspection", by J.W. Roberts, S.D.Rose, G.Jullien, L.Nichols, G.Moroscher, P.T.Jenkins, S.G.Chamberlain, R.Mantha, and D.J. Litwiller, DALSA Inc., SPIE vol. 1907, Machine Vision Applications in Industrial Inspection, 1993, pp. 7-29-7-41.

"Real-Time Computer Vision on PC-Cluster and Its Application to Real-Time Motion Capture", by Daisaku Arita, Satoshi Yonemoto, and Rin-ichiro Taniguchi, Kyushu University, Japan, 2000, pp. 205-206.

Technical Paper "The Application of a Flexible Machine Vision Architecture to the Inspection of Continuous Process Materials", by Brad Harkavy, from VISION '89 Conference, Chicago, Illinois, MS89-165, attended on Apr. 24-27, 1989.

"Flexible Circuits, Roll-to-Roll AOI" by Brian Tithecott, PC FAB, vol. 23, No. 2, Feb. 2000, pp. 26-28, 30, and 32.

"A New Design Environment for Defect Detection in Web Inspection Systems", by S. Hossain Hajimowlana, Roberto Muscedere, Graham A. Jullien, James W. Roberts, DALSA Inc.; SPIE vol. 3205, 1997, pp. 125-136.

"Parsytec HTS-2, Defect Detection and Classification Through Software vs. Dedicated Hardware", by Reinhard Rinn, Scott A. Thompson, Dr. Ralph Foehr, Friedrich Luecking, and John Torre; SPIE vol. 3645; Jan. 1999, pp. 110-121.

Wenyuan Xu et al., "Industrial Web Inspection for Manufacturing Process Understanding and Control", Proceedings of the SPIE—The International Society for Optical engineering SPIE-INT. Soc. Opt. Eng USA, vol. 3652, Jan. 1, 1999, pp. 10-20, XP002307220, ISSN: 0277-786X, Figure 1.

International Preliminary Examination Report, PCT/US2005/009741, Mar. 23, 2005, (18 pages).

HIBC Barcode for Industry and Health Care, Application Guidelines, Oct. 30, 2000, 38 pages.

* cited by examiner

APPARATUS AND METHOD FOR THE AUTOMATED MARKING OF DEFECTS ON WEBS OF MATERIAL

CROSS REFERENCE TO RELATED APPLICATION

This application is a continuation of U.S. Ser. No. 12/581,421, filed Oct. 19, 2009, now U.S. Pat. No. 7,974,459; which is a continuation of U.S. Ser. No. 10/826,995, filed Apr. 19, 2004, granted as U.S. Pat. No. 7,623,699 on Nov. 24, 2009, the disclosure of which is incorporated by reference in its entirety herein.

TECHNICAL FIELD

The present invention relates to automated inspection systems, and more particularly to a system and device for marking moving webs so as to identify the specific location of defects.

BACKGROUND

Inspection systems for the analysis of moving web materials have proven critical to modern manufacturing operations. Industries as varied as metal fabrication, paper, nonwovens, and films rely on these inspection systems for both product certification and online process monitoring. They provide value in two major areas. First, they can be used to measure and report product quality in real-time, thereby enabling continuous optimization of the manufacturing process. Second, they are used to identify defective material, enabling that material to be segregated before shipment to the customer. Unfortunately, accurate identification of defective areas can be extremely difficult depending on the nature of the web combined with the time and place of product converting.

Methods of identifying defective regions range from grading rolls using electronic maps to various marking mechanisms. Grading rolls is adequate if one wants to judge bulk statistics of the web. However, in order to remove specific defective regions the roll must be re-inspected. Markers tend to be used to mark only the web edge, and in many cases this is sufficient. Once the mark is identified on the web edge, one usually removes the defective portion. Unfortunately, there are more situations arising where edge marking of webs is not sufficient. These include:

1) Defects difficult to later identify such that even with the presence of an edge mark humans may have a very difficult time finding the defect. Wide webs and small defects compound this situation.

2) Situations where the initial roll is slit into smaller rolls such that the edge mark is no longer present on the narrower rolls.

Besides these difficulties, another concern is raised by the desirability in manufacturing to produce product "just-in-time". Manufacturing product only when customers require it allows industry to reduce its inventory of finished goods, which results in savings to consumers. However, achieving this goal often has manufacturers working to develop systems and devices that allow a rapid change over between various products.

SUMMARY OF THE INVENTION

Web inspection and defect marking fields are further benefited by the present system through which the marking is deferred from the time of inspection. This allows the identification of only those blemishes that are considered defects with respect to the contemplated end use of the web, even when that end use is selected "just-in-time," immediately prior to the final converting of the web into its finished form.

The present invention provides a system for the characterization of webs that permits the identification of anomalous regions on the web to be performed at a first time and place, and permits the localization and marking of actual defects to be performed at a second time and place. This allows the selection of what constitutes an actual defect with respect to the contemplated end-use of the web to be made "just-in-time". Material waste is reduced since the criteria of what constitutes defects that would disqualify a portion of the web for a particular end use no longer needs to be equivalent to that used for the most demanding end-use applications.

In a first aspect, the invention can be thought of as a method of analyzing the characteristics of a web of material, comprising:

imaging a sequential portion of the web to provide digital information;

processing the digital information with an initial algorithm to identify regions on the web containing anomalies;

placing fiducial marks on the web;

recording positional information localizing the identified regions relative to the fiducial marks; and applying locating marks to the web identifying the position of at least some of the anomalies, using the positional information and the fiducial marks as a guide.

In most of the convenient embodiments of the method, the position of only the anomalies that qualify as actual defects with respect to the contemplated end use of the web are identified with locating marks. In carrying out the method, it is frequently advantageous to further carry out extracting identified regions from the digital information, and analyzing the extracted identified regions with at least one subsequent algorithm to determine which anomalies represent actual defects with respect to the contemplated end use of the web. The steps are conveniently accomplished using techniques disclosed in the copending and coassigned U.S. patent application Ser. No. 10/669,197, "Apparatus And Method For Automated Inspection Of Moving Webs By Reprocessing Image Information", which is hereby incorporated by reference in its entirety.

Following the guidance of the just mentioned reference, it will frequently be advantageous to perform a storing or buffering of the identified regions prior to analyzing them, even to such an extent that the stored or buffered information is analyzed after the imaging has been performed on the entire web. When it is convenient for the user of the method to perform the identification of anomalous regions on the web at a first time and place and perform the localization and marking of actual defects at a second time and place, it will usually also be convenient to perform a winding of the web onto a roll between the placing step and the applying step. The wound roll can then be shipped to a convenient place along with the stored information about its surface anomalies, where it can there wait for a decision to be made about application of the roll to a specific end-use. Depending on the exact end-use, it may be convenient to place the locating marks on or adjacent to the anomalies whose position they identify, or it may be convenient to place the locating marks such that they are spaced in a predetermined way from the anomalies whose position they identify.

In the second aspect, the invention is a system for marking a web of material. The system includes a fiducial marker for applying fiducial marks to the web and an inspection module for imaging a sequential portion of the web to provide digital information, processing the digital information with an initial algorithm to identify regions on the web containing anomalies, and recording positional information localizing the identified regions relative to the fiducial marks. The system also includes a fiducial reader for reading and providing localizing information from the fiducial marks, a web marker for applying locating marks to the web, and a web marker controller for controlling the web marker so as to apply locating marks to the web identifying the position of at least some of the anomalies, using the positional information and the localizing information as a guide.

In a preferred embodiment, the web marker applies locating marks identifying the position of only the anomalies that qualify as actual defects with respect to a contemplated end use of the web. In such embodiments, it is advantageous to arrange for the inspection module to extract identified regions from the digital information. Then the system may further include a processor associated with the web marker controller for analyzing the extracted identified regions with at least one subsequent algorithm to determine which anomalies represent actual defects with respect to the contemplated end use of the web.

The user of the system may perform the identification of anomalous regions on the web at a first time and place and perform the localization and marking of actual defects at a second time and place. In this instance, it is usually also convenient to have the inspection module store or buffer the identified regions for the processor. In certain embodiments, the fiducial marker and the inspection module may be associated with a first web handling apparatus, and have the fiducial reader, the web marker, and the web marker controller be associated with a second web handling apparatus.

Other features and advantages will be apparent from the following description of the embodiments thereof, and from the claims.

DEFINITIONS

For purposes of the present invention, the following terms used in this application are defined as follows:

"web" means a sheet of material having a fixed dimension in one direction and either a predetermined or undetermined length in the orthogonal direction;

"fiducial mark" means a symbol or numerical identifier used to uniquely identify a particular position; "application specific" means defining product requirements based on its intended use; and "anomaly" or "anomalies" mean a deviation from normal product that may or may not be a defect, depending on its characteristics and severity.

BRIEF DESCRIPTION OF THE DRAWING

In the several figures of the attached drawing, like parts bear like reference numerals, and.

DETAILED DESCRIPTION

Figure 1:
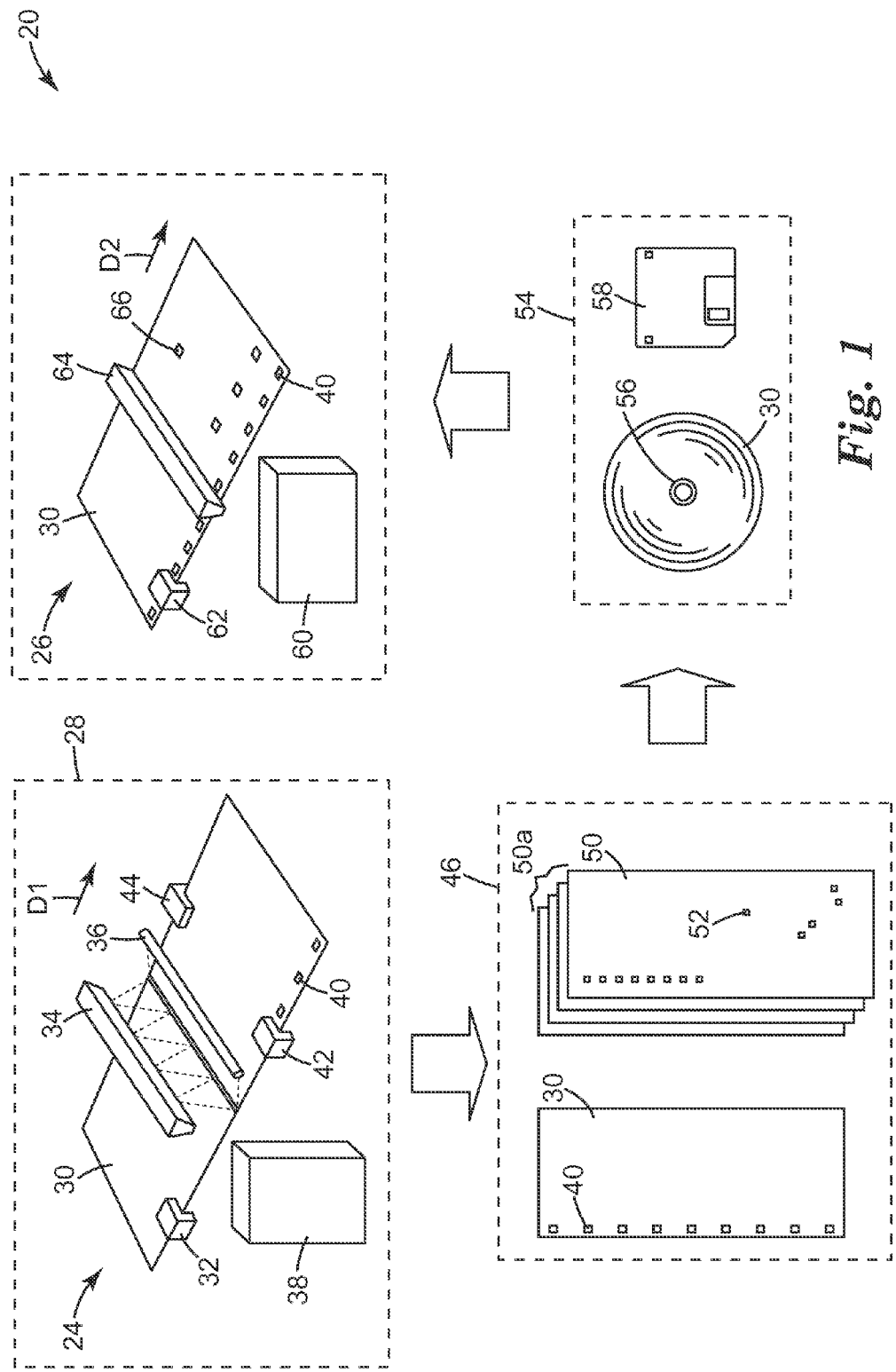
FIG. 1 illustrates a schematic view of an exemplary system according to the present invention.

Referring now to FIG. 1, a schematic view of the flow of information and material through an exemplary method 20 according to the present invention is illustrated. The Apparatus and the method 20 associated with the practice of the present invention may generally be considered as two distinct modules, an inspection module 24, and marking module 26. It is not a requirement of the invention that the inspection module 24 and the marking module 26 be separated as illustrated in FIG. 1, although many of the most preferred embodiments will be so arranged.

The process begins at a first stage 28. The inspection module 24 is adapted to act on a web of material 30 moving in direction D1. Many different sorts of web materials are suitable for use with the present invention, as will be discussed in greater detail below.

It may be preferred to provide steering for the web 30 at the beginning of the inspection module 24 and, when this is the case an edge sensor 32 may be employed, its information feeding back into any convenient web steering mechanism. The web 30 is then directed below camera 34, which is positioned so as to be able to image web 30 where it is illuminated by lighting device 36. Although the figure illustrates the web illuminated by reflected light, transmitted or transflected light may also be employed.

Digital information from the camera 34 is directed to a processor 38 which processes the digital information with an initial algorithm to identify regions on the web 30 containing anomalies. In most of the preferred embodiments, the processor 38 uses a simple initial algorithm that can be run in real-time and is at least capable of identifying regions that are anomalous. The processor 38 then extracts identified regions from the digital information for later consideration. In these embodiments, the method includes making this consideration by analyzing the extracted identified regions with at least one subsequent algorithm to determine which anomalies represent actual defects with respect to the contemplated end use of the web. This analysis can be performed by the inspection module 24, or by the marking module 26, or by a suitable intermediate module, and depending on the exact application, advantages may accrue from any of these possibilities. Regardless, it is often preferred to store or buffer the identified regions prior to analyzing.

In carrying out the method of the present invention, it is necessary to place fiducial marks 40 on the web 30 and then record positional information localizing the identified regions relative to these fiducial marks 40. The fiducial marks 40 may be placed on the web 30 prior to entering the inspection module 24, in which case the processor 38 may be programmed to make note of them when they are imaged by camera 34. Alternatively, and as depicted in FIG. 1, the fiducial marks 40 may be added to the web 30 by a fiducial marker 42 and integrated by the processor 38 into the positional information in an alternative manner. Whether the step of placing fiducial marks 40 on the web 30 is done before or after the step of imaging the web 30, the processor 38 records positional information localizing the identified regions relative to the fiducial marks 40.

For some specialized end uses for the web 30, it may be preferred to place along the web's edge some mark corresponding to the location of either anomalies or identify defects. If this is the case, optional lateral marker 44 may be used to apply such marks.

Once the web 30 has passed through the inspection module 24, an intermediate stage 46 has been reached. At this point, the web 30 has been marked with fiducial marks 40, and at least one electronic map 50 (conceptualized in the Figure as a corresponding object) has been created to record positional information localizing the identified regions (conceptualized in the Figure with reference numeral 52) relative to the fiducial marks 40. At least one electronic map 50 will exist, and possibly more than one (collectively 50*a*). More than one electronic map may exist if either the initial algorithm, or the optional subsequent algorithm(s) have at this time determined which anomalies represent actual defects with respect to more than one contemplated end use of the web.

In most preferred embodiments of the present invention, a second intermediate stage 54 will be reached wherein the web 30 has been wound on a core 56 for shipping to a convenient location for accomplishing the conversion of the web 30 into a form useful for a contemplated end use. Electronic maps 50 and/or 50*a* are also transmitted to the location where the conversion will be performed, illustrated in the figure in stylized form as a diskette 58, although any convenient means of electronic transmission can be used.

Regardless of whether optional intermediate stage 54 has occurred, the web 30 is placed in motion in direction D2 into a marking module 26. A web marker controller 60 is provided with at least one of the corresponding electronic maps 50 corresponding to that particular web 30. The web marking controller 60 addresses the optional step of analyzing the electronic map 50 with a subsequent algorithm(s) to determine which anomalies represent actual defects with respect to the now contemplated end use of the web.

The web 30 is first passed through a fiducial reader 62 for reading and providing localizing information from the fiducial marks 40. The fiducial reader 62 communicates this localizing information to the web marker controller 60. The web marker controller 60 executes a program to form a plan to apply locating marks to the web identifying the position of at least some of the anomalies, using the positional information and the localizing information as a guide. The web marker controller then sends a series of commands to a web marker 64, which then applies locating marks 66 to the web 30. In keeping with the discussion above, in most embodiments of the invention only those anomalies that qualify as actual defects with respect to the contemplated end use of the web are identified with locating marks 66. In many preferred applications of the present invention, the locating marks 66 are on or adjacent to the anomalies whose position they identify. However, in some specialized applications the locating marks 66 are spaced in a predetermined way from the anomalies whose position they identify.

Figure 2:
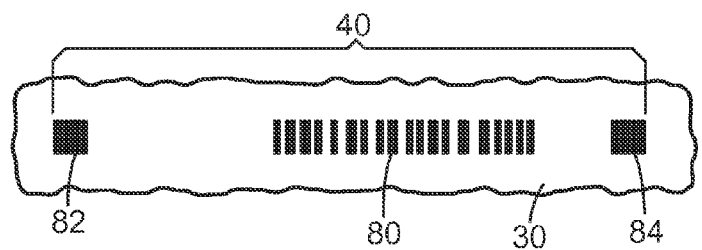
FIG. 2 illustrates a convenient form for a fiducial mark used in connection with the present invention.

Referring now to FIG. 2, a convenient form for a fiducial mark 40 used in connection with the present invention is illustrated. These marks are placed at regular intervals throughout the length of the web. The complete fiducial mark 40 includes one or more fiducial locating marks 82,84 which exactly locate a particular position within the web and a barcode 80 which conveniently encodes a unique identifier for each fiducial locating mark 82,84. Thus, the fiducial marks 82,84 accurately locate a position and the barcode uniquely identifies that position so that the electronic map can be re-synchronized to the physical web during the marking operation.

Figure 3:
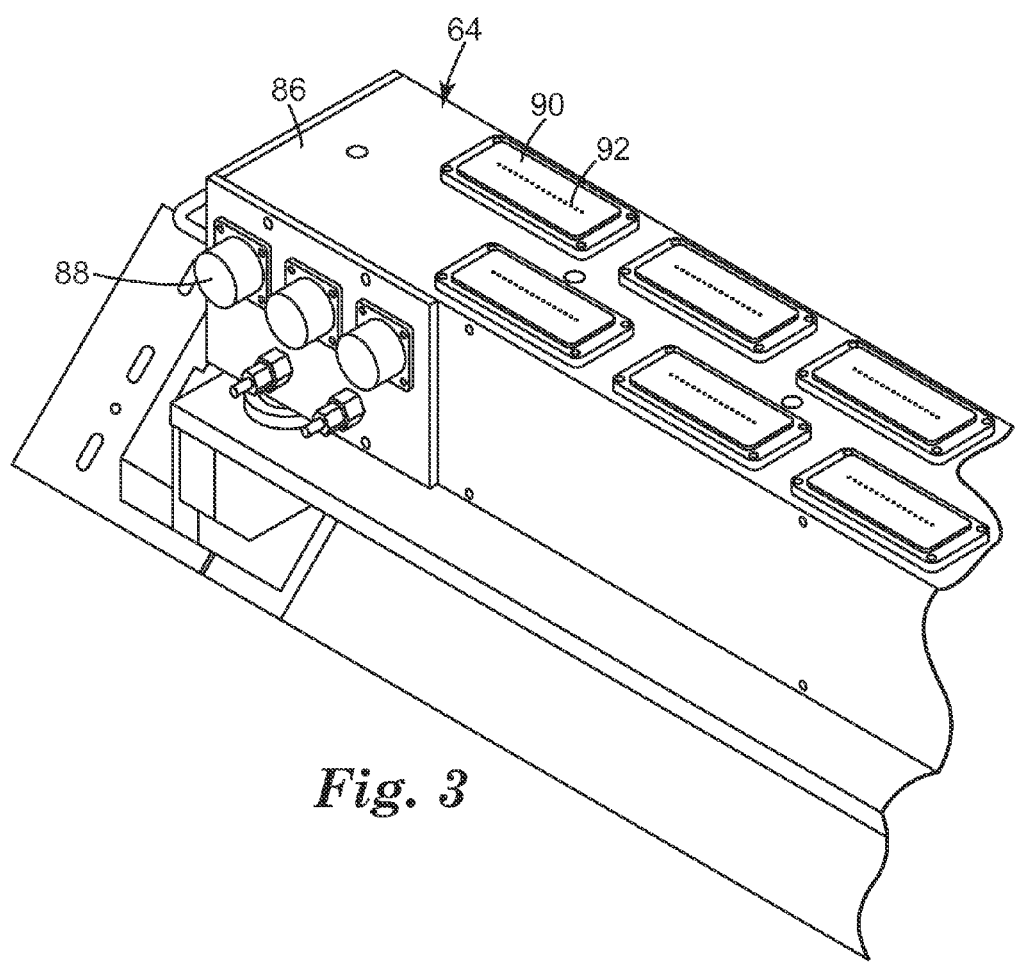
FIG. 3 illustrates a perspective view of a portion of a web marker suitable for use in connection with the present invention.

FIG. 3 is a perspective view of a portion of one example of a web marker 64 suitable for use in the present invention. The web marker 64 includes a frame 86 and mounting cable connectors 88 for communication with other apparatus including the web marker controller 60 (not shown). Also mounted on the frame 86 are a series of ink jet modules 90, each having a series of jet nozzles 92 thereon. The ink-jet modules 90 are conveniently mounted in staggered position in two rows so that coverage across the width of even a wide web can be provided in such a way that a malfunction can be addressed by the replacement of the single errant ink-jet module 90, rather than disassembly of the entire mechanism. The actual operating mechanics of the ink-jet modules 90 is conventional as understood by practitioners in an art.

Web Materials

In accordance with the present invention, the continuously moving web may include any sheet-like material that has a predetermined width and thickness and either an undetermined or predetermined length. Materials provided in web form that may be optically imaged are suitable for use with the present invention. Examples of web materials include, but are not limited to, metals, paper, wovens, non-wovens, glass, polymeric films or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

One type of inspection problem particularly suitable to resolution through use of the present invention is the inspection of optical films. With films intended for, e.g. the surface of a computer display, where subtle defects can loom large to a user who is looking at the display for hours at a time. Sometimes defining exactly what sort of defect in this sort of application will be unacceptably burdensome to the user, and what sort of defect is harmless is quite complex. A scheme for reducing the complexity of the determination is presented with more particularity below.

A second type of inspection problem is the inspection of flexible circuit webs. The invention is particularly suited for dealing with the complexity involved where individual circuits on a flexible circuit web have repeating circuit patterns deposited or formed on a flexible substrate. A web typically has multiple individual circuits each including various small parts arranged in arbitrary patterns. The individual circuits are later separated from the web by e.g. die cutting for use in discrete electrical applications.

For many applications suited for the present invention, the web materials or combined materials may preferably have an applied coating. Coatings that may be optically imaged are suitable for use with the present invention. The coatings are generally applied to an exposed surface of the base web material. Examples of coatings include adhesives, optical density coatings, low adhesion backside coatings, metalized coatings, optically active coatings, electrically conductive or nonconductive coatings, or combinations thereof. The coating may be applied to at least a portion of the web material or may fully cover a surface of the base web material.

Image Acquisition

The image acquisition is accomplished through the use of conventional imaging devices that are capable of reading a sequential portion of the moving web and providing output in the form of a digital data stream. For purposes of the invention, the imaging device may include a camera that directly provides a digital data stream or an analog camera with an additional analog to digital converter. Furthermore, other sensors, such as for example, laser scanners may be utilized as the imaging device. A sequential portion of the web indicates that the data is preferably acquired by a succession of lines. The lines comprise an area of the continuously moving web that optically map to one or more rows of sensor elements or pixels. Examples of devices suitable for acquiring the image include linescan cameras such as Model#LD21 from Perkin Elmer (Sunnyvale, Calif.), Piranha Models from Dalsa (Waterloo, Ontario, Canada), or Model#TH78H15 from Thompson-CSF (Totawa, N.J.). Additional examples include laser scanners from Surface Inspection Systems GmbH (Munich, Germany) in conjunction with an analog to digital converter.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process.

Anomaly or Defect Detection

After acquisition, images are processed using either conventional defect detection processing or using techniques disclosed in the copending and coassigned U.S. patent application Ser. No. 10/669,197, "Apparatus And Method For Automated Inspection Of Moving Webs By Reprocessing Image Information", which has been previously incorporated by reference in its entirety. The latter technique generally employs a system that performs a preliminary examination with a first, typically less sophisticated algorithm. The preliminary examination produces image information about the regions of the web containing anomalies. Some of the anomalies will be defective, but many could be "false positives", or anomalies that are not defective. In fact, some areas may be defective if the product is used in a particular application, but not defective if it is used in another. To effectively separate actual defects from anomalies, the original image information is reconsidered later and subjected to at least one of a variety of more sophisticated image processing and defect extraction algorithms.

Defect detection algorithms or anomaly detection algorithms employed in the present invention include those conventionally utilized in the field of web inspection. Those skilled in the art of establishing web inspection systems are cable of matching one or more algorithms with specific web and defect types to achieve a desired accuracy level of defect detection. Non-limiting examples of suitable algorithms include neighborhood averaging, neighborhood ranking, contrast expansion, various monadic and dyadic image manipulations, digital filtering such as Laplacian filters, Sobel operators, high-pass filtering and low-pass filtering, texture analysis, fractal analysis, frequency processing such as Fourier transforms and wavelet transforms, convolutions, morphological processing, thresholding, connected component analyses, blob processing, blob classifications, or combinations thereof.

In a preferred embodiment, anomaly detection is employed at a first stage of the process using a selected algorithm to produce an electronic map. The web of material is wound up into a final roll during this processing step. The electronic map and the web are subsequently inspected in light of a desired end use. The anomalies that are truly defects for the desired end are identified on the web with location marks, as further described below.

Anomaly or Defect information extracted from the image information is saved in a convenient data storage mechanism for later transfer and utilization in the marking process. Examples of storage mechanisms include various computer file and database formats. A preferred method utilizes a database such as Microsoft SQL Server from Microsoft Inc., Redmond, Wash.

Fiducial Marking

The fiducial marks and associated barcodes may be imprinted on the web material using many different methods including ink marking, laser printing, mechanical impressioning devices, or other similar methods. It is important that the marks can be reliably applied and production web speeds and that the marks are easily sensed and the barcodes easily read during successive operations. An example of a suitable printing device is Model 6800 Ink Jet Printer from Linx Printing Technologies (Cambridgeshire, UK) and a suitable barcode reader is Model 530 from DVT Corporation (Duluth, Ga.).

Defect Location Marking

At some time after the initial inspection and application of fiducial locating marks, the product's defects as determined by the inspection system can be marked so as to allow for easy identification and removal. Depending on the web material and production conditions, many different marking mechanisms and marking configurations may be appropriate. However, methods of marking preferably have the capability of applying the defect mark sufficiently close the to the location of the actual product defect on the web. Arrayed markers have proven particularly effective, but position controlled markers are also suitable. A particularly convenient method for film products utilizes an array of ink markers such as model MS610 from Matthews of Pittsburgh, Pa.

As the web passes through the system during the marking operation, fiducial marks are regularly sensed and associated barcodes read. The combination of barcode and fiducial mark enables one to precisely register the physical position of the web to the anomalies or defects identified in the electronic map. Regular re-registration ensures ongoing registration accuracy. One skilled in the art is capable of establishing the re-registration through conventional physical coordinate transformation techniques. Since the physical web is now registered to the electronic map, the physical position of specific anomalies or defects is known. In the instance where the physical position of defects or anomalies subsequently identified as true defects pass under the marking unit, marks are applied to the web. The type of mark and the exact position of the mark on or near the defect may be selected based upon the web material, defect classification, web processing required to address the defect, and the intended end use application of the web. In the case of the arrayed ink marker, markers are fired preferentially depending on their crossweb position as defects pass the unit in the downweb direction. With this method, marking accuracies of less than 1 mm have been regularly achieved on high-speed webs with production rates greater than 150 ft/minute. However, higher speed webs in excess of 1000 meter/minute are within the capability of the invention.

EXAMPLE 1

A model 6800 Lynx printer was adapted to print along the edge of a web so as to serve as a fiducial marker, and was used to print fiducial marks on a moving polymeric web. Each of these fiducial marks included a bar-code and a fiducial position generally as depicted in FIG. 2. The polymeric web was formed from transparent polyester 5 mils thick, commercially available from 3M Company, St. Paul, Minn.

The web, bearing its fiducial marks, was then directed to an inspection module that imaged sequential portions of the web. This imaging was accomplished by a model AT71XM2CL4010-BA0 camera, commercially available from Atmel of San Jose, Calif. The web was viewed backlit by a lighting module commercially available from Schott-Fostec, LLC, of Alexandria, Va. Digital information from the camera was sent to a model Precision 530 digital computer, commercially available from Dell Computer Corp. of Round Rock, Tex. There it was processed with an initial algorithm to identify regions on the web containing anomalies. The camera also brought to the digital processor information concerning the fiducial marks. The digital processor then extracted information concerning the identified regions and recorded positional information localizing the identified regions relative to the fiducial marks. The positional information was stored to magnetic media, and the web was wound onto a spool for later processing.

EXAMPLE 2

The web of example 1 was placed in motion, unwinding from its spool in the reverse direction from which it was wound. It was directed past a fiducial reader including a model Legend 530 camera, commercially available from DVT of Duluth, Ga. Positional control over the web as it passed by the fiducial reader was provided by a servo position controller commercially available from Accuweb of Madison Wis., based on information from the web edge sensor commercially available as model 1.5X3U 4043-01, also from Accuweb. The illumination of the web at the fiducial reader was provided by a backlight module commercially available from Advanced Illumination of Rochester, Vt. The output of the camera was directed to a web marker controller comprising a model Precision 530 digital computer, commercially available from Dell Computer Corp., so that information localizing the fiducial marks on the web could be obtained.

The processor in the web marker controller was also provided with the recorded positional information obtained in Example 1. The web marker controller combined in the recorded positional information with the localizing information from the fiducial reader to form an electronic map of the location of web anomalies.

The web was then directed under a web marker generally constructed as depicted in FIG. 3. In this web marker, ink jet modules commercially available as model MS610 from Matthews of Pittsburgh, Pa. were mounted on a frame in two staggered rows and were placed under the control of the web marker controller. When according to the electronic map of web anomalies, an anomaly was passing under the web marker, a small jet of black ink was expelled from the appropriate jet module onto the web to identify the location of the anomaly. During some runs, the web marker controller was programmed to direct the web marker to place a mark adjacent the web edge at the predictable distance in a machine direction sense compared to the anomaly. In other experiments, the mark was placed directly on the anomaly. In these latter cases, during the rewind of webs up to 2000 meters in length, positional accuracy errors in placing the mark on the anomaly of no more than 1 mm was obtained.

EXAMPLE 3

The web according to Example 1 was moved and marked generally according to description in Example 2, except that the web marker controller was provided with a subsequent algorithm designed to use distinguish actual defects rendering that portion of the web unsuitable for a particular contemplated end-use from other anomalies among the extracted information in the electronic map. During the run, the web marker controller was further programmed to send commands to the web marker to place locating marks on only those anomalies that qualified according to the subsequent algorithm as actual defects.

Various modifications and alterations of the present invention will be apparent to those skilled in the art without departing from the scope and spirit of this invention, and it should be understood that this invention is not limited to the illustrative embodiments set forth herein.

The invention claimed is:

1. A method of analyzing a web of material containing at least two anomalies, comprising:
    receiving the web of material having upon it regularly spaced fiducial marks that uniquely identify a plurality of distinct positions on the web;
    receiving digital information that identifies regions on the web containing the at least two anomalies, and positional information defining the positions of the identified regions relative to at least one of the fiducial marks; and
    as part of a web operation that is temporally distinguished from web operations that yielded the digital information and separated by at least a winding step whereby the web of material is wound onto a roll, unwinding the web and applying locating marks to the web identifying the position of at least one of the identified regions, using the positional information and the fiducial marks as a guide.

2. The method according to claim 1, further comprising:
    storing or buffering the digital information describing the identified regions;
    receiving input defining the constituents of an anomaly that is a defect with respect to a contemplated end use of the web;
    processing the digital information describing the identified regions to identify at least one identified region that qualifies as an actual defect with respect to the contemplated end use of the web, and to identify at least one identified region that does not qualify as an actual defect with respect to the contemplated end use of the web;
    and wherein the locating mark is applied to identify the position of only the at least one identified region that qualifies as an actual defect with respect to the contemplated end use of the web.

3. The method according to claim 2 wherein:
    processing the digital information describing the identified regions comprises analyzing the identified regions with an algorithm to determine at least one identified region that qualifies as an actual defect with respect to the contemplated end use of the web, wherein the algorithm is not the same as any that might have been used to determine the identified positions.

4. The method according to claim 2 wherein the locating marks are on or adjacent to the anomalies whose position they identify.

5. The method according to claim 2 wherein the locating marks are spaced in a predetermined way from the anomalies whose position they identify.

* * * * *

UNITED STATES PATENT AND TRADEMARK OFFICE
CERTIFICATE OF CORRECTION

| | | |
|---|---|---|
| PATENT NO. | : 8,238,646 B2 | Page 1 of 1 |
| APPLICATION NO. | : 13/102434 | |
| DATED | : August 7, 2012 | |
| INVENTOR(S) | : Steven Paul Floeder | |

It is certified that error appears in the above-identified patent and that said Letters Patent is hereby corrected as shown below:

Column 5

Line 61; delete "inkjet" and insert -- ink-jet -- therefor.

Column 6

Line 65; delete "Totawa" and insert -- Totowa -- therefor.

Column 8

Line 12; delete "close the to" and insert -- close to -- therefor.

Signed and Sealed this
Twenty-third Day of October, 2012

David J. Kappos
*Director of the United States Patent and Trademark Office*